(12) United States Patent
Chen et al.

(10) Patent No.: US 8,287,732 B2
(45) Date of Patent: Oct. 16, 2012

(54) INTEGRATION OF ANAEROBIC DIGESTION IN AN ALGAE-BASED BIOFUEL SYSTEM

(75) Inventors: Shulin Chen, Pullman, WA (US); Craig Frear, Pullman, WA (US); Quanbao Zhao, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 106 days.

(21) Appl. No.: 12/906,573

(22) Filed: Oct. 18, 2010

(65) Prior Publication Data

US 2011/0091954 A1    Apr. 21, 2011

Related U.S. Application Data

(60) Provisional application No. 61/252,477, filed on Oct. 16, 2009.

(51) Int. Cl.
*C02F 3/32* (2006.01)
*C02F 3/00* (2006.01)
*C02F 9/00* (2006.01)
*C05F 11/08* (2006.01)

(52) U.S. Cl. ........ 210/602; 210/603; 210/614; 210/259; 71/10

(58) Field of Classification Search .................. None
See application file for complete search history.

(56) References Cited

U.S. PATENT DOCUMENTS 7,927,491 B2 *    4/2011    Kotelko et al. ................ 210/602

OTHER PUBLICATIONS

Hong-Wei Yen et al.; "Anaerobic co-digestion of algal sludge and waste paper to produce methane"; Bioresource Technology 98 (2007); pp. 130-134.
Golueke et al.; "Anaerobic Digestion of Algae"; Applied Microbiology, Jan. 1957; 5(1): pp. 47-55.
Sialve, B., et al., "Anaerobic digestion of microalgae as a necessary step to make microalgal biodiesel sustainable," Biotechnology Advances 27 (2009) 409-416.
Heaven, S., et al., "Comments on 'Anaerobic digestion of microalgae as a necessary step to make microalgal biodiesel sustainable'," Biotechnology Advances 29 (2011) 164-167.

* cited by examiner

*Primary Examiner* — Suzanne M Noakes
*Assistant Examiner* — Jae W Lee
(74) *Attorney, Agent, or Firm* — Whitham, Curtis, Christfferson & Cook, P.C.

(57) ABSTRACT

Systems and methods for the treatment of lipid-extracted algae biomass and recycling nutrients are provided. The lipid-extracted algae biomass is hydrolyzed prior to anaerobic digestion, and the products generated by anaerobic digestion are further processed to yield by-products that are of use either for external use or as process inputs to carry out specific steps within an integrated algal growth and anaerobic digestion process designed to minimize economic costs, required costly inputs while improving upon system capabilities.

14 Claims, 4 Drawing Sheets

INTEGRATION OF ANAEROBIC DIGESTION IN AN ALGAE-BASED BIOFUEL SYSTEM

CROSS-REFERENCE TO RELATED APPLICATIONS

This application claims benefit of U.S. provisional patent application 61/252,477, filed Oct. 16, 2009, the complete contents of which are hereby incorporated by reference.

BACKGROUND OF THE INVENTION

1. Field of the Invention

The invention generally relates to the recovery of nutrients during the treatment of lipid extracted algae waste to particular, the invention provides an economical, integrated system for the recovery of nutrients and other by-products from hydrolysis and digestion of lipid extracted algae waste and for their re-use in algae growth or other systems.

2. Background of the Invention

With many technical and resource challenges remaining, there is a general consensus that algae have the most potential for significant portion of crude oil displacement among all the known biomass. According to Chisti (*Biodiesel from Microalgae, Biotechnology Advances.* 25 (2007):294-306), it takes approximately 1.1% and 2.5% of existing US cropping area to meet 50% of all transportation fuel needs of the United States assuming 70% and 30% of oil in dry algae biomass, respectively. If used as a means for $CO_2$ sequestration, 1.6-1.8 lb of $CO_2$ will be fixed for each lb of algae biomass produced. Consuming each lb of algae-based biofuel will reduce 3 lbs of $CO_2$ release associated with burning the same amount of fossil fuel. According to the Department of Energy "Roadmap", commercial algal growth processing could result in the co-generation of about 190 million tons of lipid-extracted biomass per year if the diesel consumption of the US were replaced by algal lipid based biofuel. Therefore, developing a feasible technology for converting the biomass to a product that has great demand is critical for the establishment of this industry.

Due to anticipated large amount of biomass associated with algae fuel production, there are most likely several options for the utilization of the lipid-extracted spent biomass. The first one is direct conversion of the biomass after oil extraction into biogas through the process known as anaerobic digestion (AD), a process in which complex organic materials are biologically degraded into mainly methane, $CO_2$, ammonia nitrogen (N), inorganic phosphorous (P) and other minor components. The second one is direct gasification/pyrolysis of the biomass into syngas or bio-oil; the third one is to use the biomass as animal feed; and the last one is to fractionate and separate the polysaccharides of the cell walls (mainly cellulose) for further hydrolysis into fermentable sugar to be used to produce fuel such as ethanol or hydrocarbons. There are other options such using the spent biomass for animal feed and as raw materials to produce so-products for industrial purposes. Such options requires further developments of special technologies for proper separation of algae lipid from the rest of the algal biomass.

Among all these options, AD appears to be the most feasible. First, AD is a relatively low-cost technology that is well suited for treating wet organic materials. Second, AD can facilitate recovery of nutrients, principally nitrogen and phosphorous whose sustainable supply is critical to the success of large-scale algal fuel production. Recovering nutrients for recycling has great importance as growing the required algae biomass needs a tremendous amount of fertilizers. Manufacturing N fertilizer is very energy intensive. Additionally, P fertilizer is a non-renewable resource that has finite supply. AD technology fits well within these requirements and limitations and brings multiple benefits as it allows for total recovery of the energy and materials and minimizing the input to the system. In the scenario when the residue biomass is used as animal feed, the same AD process can be employed at the animal farm to recover the carbon and nutrients from the animal manure.

Although AD as a process for organic waste stabilization has been widely used, none of the existing AD technologies is adequate for dealing with the waste that is produced nor has a systematic integrated approach to introducing the AD process into the particularities of an algae growth process been developed. Many in the industry simply attempt to introduce the AD effluent directly into the algal growth systems. However, direct inclusion of the colored, colloidal, pathogen contaminated effluent is quite inappropriate for use in an algal growth system as it results in considerable photo-inhibition and contamination, and requires considerable resources for handling the water in the effluent. On the other hand, recognition and resolution of these concerns for secondary treatment with traditional wastewater treatment processes can be very costly. What is required is a transformative technology that can overcome the described concerns present within AD effluent while reducing cost inputs through effective system design and integration.

SUMMARY OF THE INVENTION

The present invention provides a flexible, integrated system for the utilization of various outputs and in particular a method for the recovery of nutrients residing in the effluent from the anaerobic digestion (AD) of lipid extracted algae waste no mass. The method involves the treatment of lipid extracted biomass (i.e. the waste that is left over after lipids and/or oils or other products are extracted from algae) using several steps which, in one embodiment, result in the recycling of all components of the waste into a single integrated algae growth processing system which generates little or no waste. In contrast to prior art systems, in the system of the invention all components are utilized either by recycling them into an algae growth system, into a hydrolysis step, into an AD step, into a nutrient recovery step, or for other purposes. Therefore, little or no actual waste is produced by the System and methods of the invention, since each "waste" product is utilized as a substrate or ingredient in another process, advantageously another process within an algae growth system. In addition, the system and method avoid the costs associated with chemical additions being required and the costs and requirements associated with large water handling systems.

DETAILED DESCRIPTION

The present invention provides systems and methods for the treatment and use of the left-over waste biomass produced when lipids are extracted from algae. The systems and methods advantageously reuse (recycle, feedback, etc.) all products/byproducts/waste materials from each stage or step so that in the end, little or no true "waste" is produced and thus the disposal of unused waste is minimal or non-existent.

Figure 1:
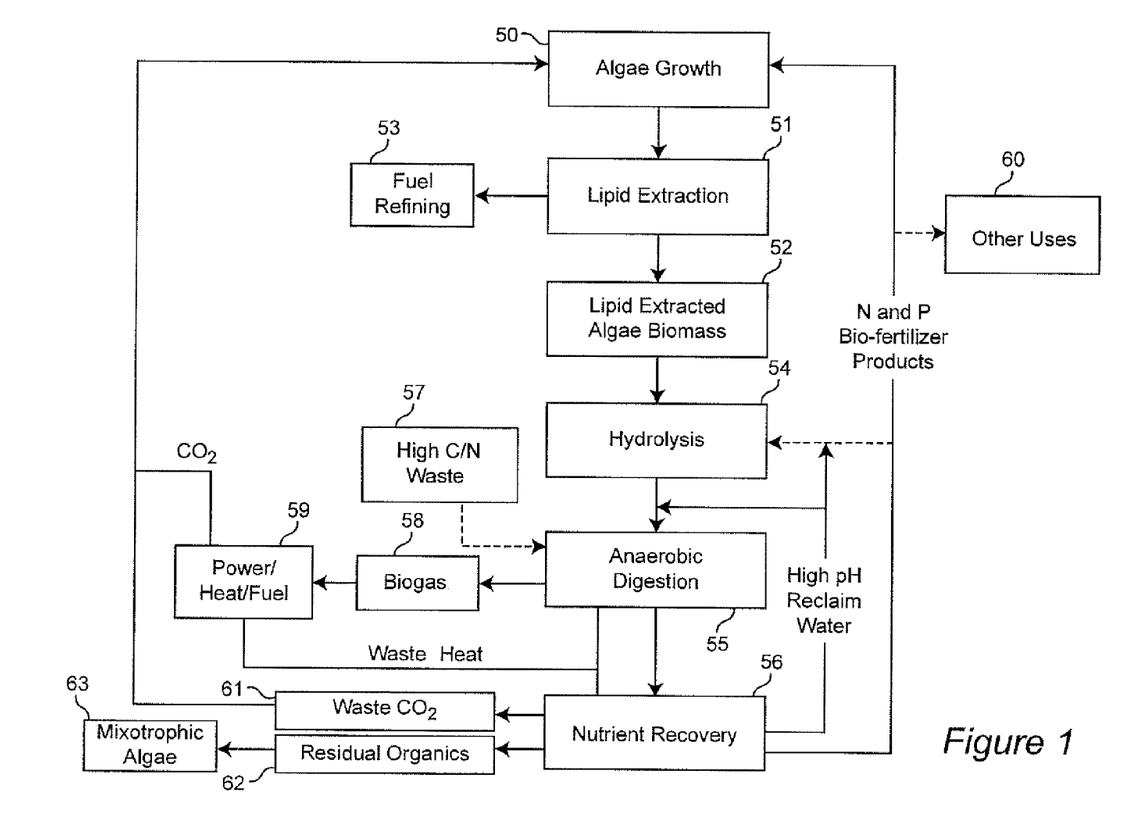
FIG. 1. Schematic representation depicting the lipid extracted algae waste treatment process of the invention.

FIG. 1 illustrates the lipid-extracted treatment methods of the invention, as integrated into an exemplary algae grow system. As can be seen in FIG. 1, algae growth 50 is followed by lipid extraction 51, the "waste" product of which is lipid extracted algae biomass 52. Extracted lipids undergo fuel refining 53, and lipid extracted algae biomass 52 undergoes hydrolysis 54, followed by anaerobic digestion 55, which is in turn followed by nutrient recovery 56. Other high C/N waste 57 can be added to anaerobic digestion 55, which produces biogas 58 used for the generation of power/heat/fuel 59. Nutrient recovery 56 produces reclaimed water (e.g. high pH reclaimed water, which is recycled into hydrolysis 54 and/or anaerobic digestion 55; and N and P bio-fertilizer products which are recycled back into algae growth, or used for other purposes (shown as other uses 60. Nutrient recovery 56 also produces waste $CO_2$ 61, which (together with waste $CO_2$ from power/heat/fuel 59 generation, is recycled back in algae growth 50. Nutrient recovery 56 also produces residual organics 62, Which are further processed using mixotrophic algae 63.

The method of the invention thus involves AD of the algae biomass; but, in contrast to prior art, preferably before entry to AD the algae waste is hydrolyzed to convert cellular polysaccharides and proteins to simpler carbohydrates, sugars, peptides and amino acids. The hydrolysis products are then fed into an AD unit, where the simple organic molecules are converted to biogas and inorganic nutrients. Optionally, during this AD step, other sources of waste (e.g. other high carbon/nitrogen ratio waste) may also be fed into the AD, together with the hydrolyzed algae biomass, thereby providing a route for recycling other waste products as well and improving upon total biogas production, biogas production efficiency and inorganic nutrient accumulation. The biogas produced in the process can then be converted to power, heat and/or fuel through a combination of known and commonly practiced unit operations involving among others engine/generator sets with heat recovery (combined heat and power systems (CHP), boiler systems, and fuel cleaning and compression systems for generation of compressed liquid fuel. Although several known hydrolysis processes could be utilized for this purpose (dilute acid pretreatment, lime (basic) pretreatment, ammonia recycle percolation, and enzymatic treatment, etc. Liao et al., 2004; Klinke et al., 2002; Kim et al., 2003; Sun and Cheng, 2002), the preferred method in this embodiment is a modified aqueous ammonia soaking that integrates well within the envisioned algal AD system through recycle of outputs from downstream operations involving nutrient recovery. As with most AD outputs, the resulting AD effluent is high in inorganic nitrogen, specifically ammonia, as well as amorphous phosphate colloidal salts bound in particular with calcium and magnesium ions. Residual organic carbon not processed during the limited AD residence time also is retained within the effluent. Also during the AD process, a considerable portion of the produced $CO_2$ gas is stored in solution as dissolved gas and bicarbonates, which along with the ammonia and inorganic phosphorous result in the support of important buffer systems and elevated levels of alkalinity (Frear et al, 2010). While inclusion of these chemical constituents (ammonia, phosphorous salts, bicarbonates, alkalinity) through direct insertion of effluent into an algal growth process can supply valued and needed nutrients to the biological growth process, as alluded to earlier, more focused inclusion of just the targeted chemical constituents as opposed to the entire effluent stream is desirable, thus requiring a unit operation for separation and recovery of nutrients as provided in the present invention.

While numerous wastewater technologies exist for the separation and recovery of chemical constituents from municipal wastewater, the techniques have been shown to be economically impractical when applied to farm-based operations due to a dual combination of unit operation capital/operating costs and a lack of due diligence in designing processes to the unique constraints and properties of non-municipal waste streams such as algae biomass (Frear et al, 2010). The present invention provides an integrated process that specifically addresses and utilizes the unique chemical constituency of algae AD effluent to cost effectively separate and recover nutrients, specifically ammonia in the form of ammonia salts (e.g. ammonia sulfate, etc.) and P-rich solids composed of phosphate salts in combination with residual organics (Frear et al, 2010).

In short, the process works by applying Henry's law and carbonate equilibrium reactions, whereby insertion of ambient air at elevated temperatures (waste engine heat) drives out and strips $CO_2$ according to the following equations:

$$CO_3^{2-}+H_2O \rightarrow HCO_3^-+OH^- \quad (1)$$

$$HCO_3^-+H_2O \rightarrow H_2CO_3+OH^- \quad (2)$$

$$H_2CO_3 \rightarrow H_2O+CO_2(l) \quad (3)$$

$$CO_2(l) \rightarrow CO_2(g) \quad (4)$$

Figure 2A:
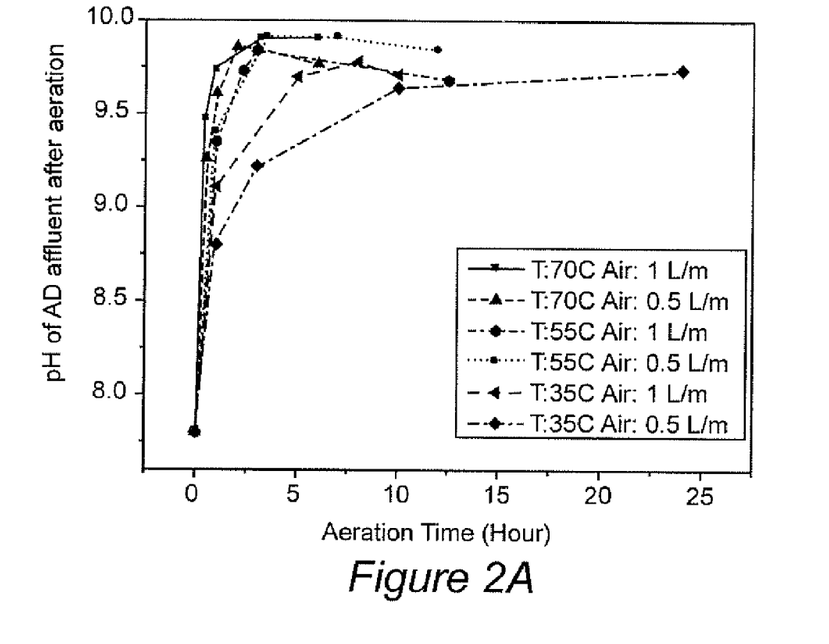
FIG. 2. Effect of aeration time, rate and temperature on (a) pH, (b) ammonia removal, and (c) Total phosphorous (TP) removal.
Figure 2B:
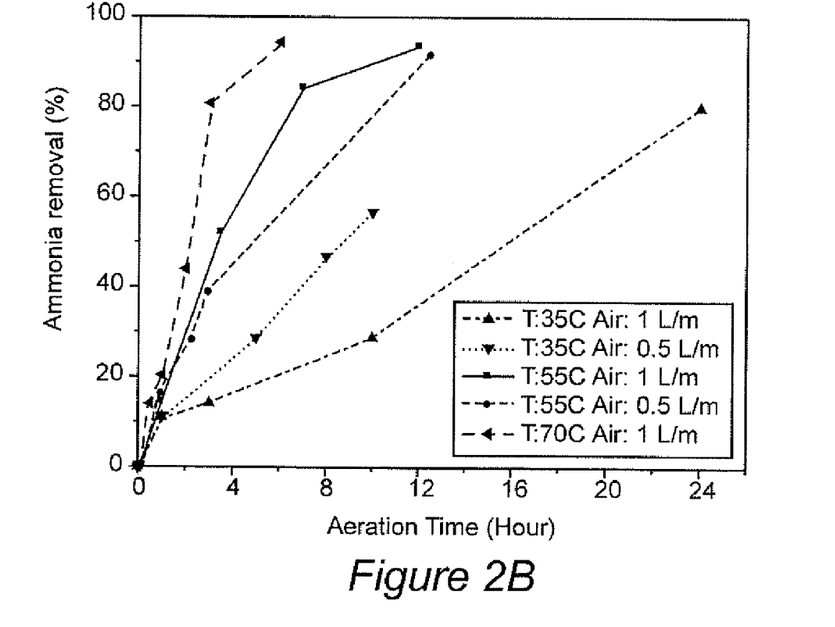
Figure 2C:
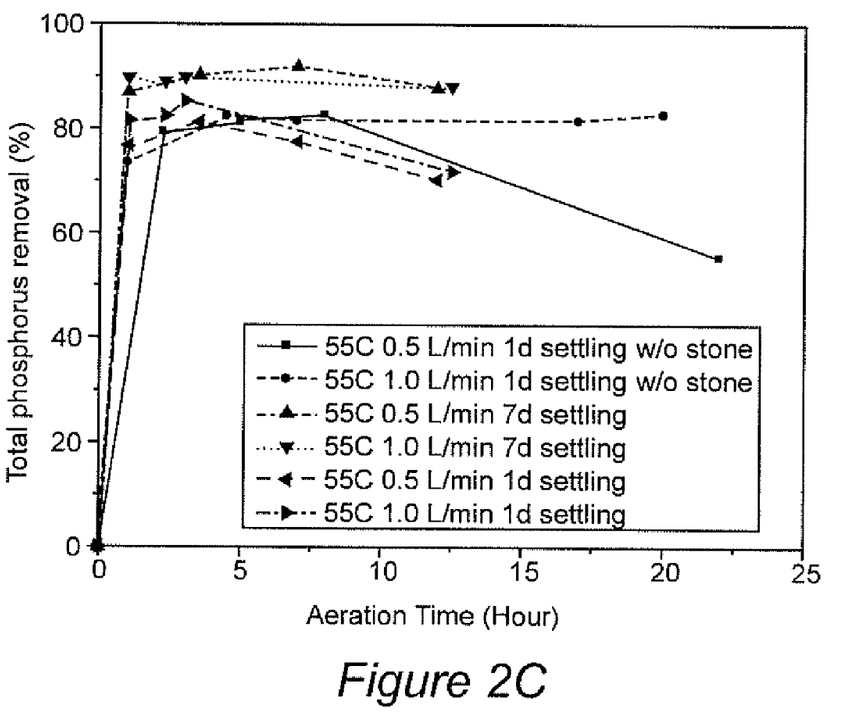

Analysis of the chemical balance shows that as aeration releases the gaseous $CO_2$, the reactions all move towards the right, generating more $OH^-$ and raising the pH of the solution, especially with elevated solution temperature. Subsequent testing of this process showed that pH in the range of 10.0 can be achieved with limited aeration. Such a pH allows for significant shifting of the ammonia equilibrium in favor of free or gaseous ammonia which could be recovered through common stripping and acid treatment methods. Importantly, the release of super-saturated gases allows for a more ready settling of P-rich colloidal solids that heretofore remained suspended mostly due to the interference of buoyant and adhesion forces associated with the gases present in solution. Thus, simple, limited aeration treatment with elevated temperatures not only leads to the desired R-settling but also N removal through the associated stripping and assumed recovery of the ammonia fraction of the N in the effluent—yielding a truly integrated nutrient recovery process. Notably, the process requires no chemical input; instead relying solely on aeration and temperature, both of which can be supplied using only waste engine exhaust heat and parasitic electricity from the digester (FIG. 2). As shown in FIG. 2A, when a similar system is aerated with ambient air, the pH increases substantially, significant amounts of ammonia are removed (FIG. 2B) and about 80-90% of the total phosphorus is removed by natural settling for one day to 7 clays after aeration.

Although well integrated as a stand-alone nutrient recovery system as applied to AD in general, the process has important and unique additional integrations as it applies to algal biomass growth systems. As noted earlier, in one embodiment of the invention, the bio-fertilizer products produced during the nutrient recovery process are directly applied to growth facilities at agronomic concentrations, and rates, not requiring the simultaneous inclusion of wastewater potentially contaminated with pathogenic and phototrophic inhibitors. In addition, during the production of the ammonia sulfate bio-fertilizer salts through use of acid reaction towers, un-reacted $CO_2$ leaves the towers as a contained hot exhaust flow. This $CO_2$ exhaust along with additional engine $CO_2$ exhaust from the AD engine systems can be incorporated into the algal growth systems as phototrophic carbon feed to the microorganisms, thus maximizing the re-use and sequestering of $CO_2$ resources within the system, in turn increasing carbon sequestration and reducing impact on global climate change. In addition, a liquid effluent, strongly reduced in solids, carbon, nitrogen, phosphorous and pathogen content, but still containing reduced but important levels of these chemicals, and of note, alkalinity, is available for partial return to algal growth systems for use as nutrient and bicarbonate rich reclaim water, albeit at significantly reduced levels of inhibitors, especially those resulting in photo-inhibition.

Of great importance is the aforementioned concept of utilizing nutrient recovery outputs for operation of the hydrolysis unit. A portion of the nutrient recovery effluent (that which is not being returned to the algal growth facilities) can be sent back to the hydrolysis and AD units to assist in hydrolysis as well as dilution of algal solid content to required to percentages preferred by particular AD operations in regard to hydrolysis, high temperature (50-70 C) and high pH liquid effluent (in the range of from about 9 to 11, and usually ~10.0) from the nutrient recovery system is placed in the hydrolysis reactor with a portion of un-reacted, but stripped ammonia that had not sent to the acid towers. The result is a modified aqueous ammonia soaking system capable of effective hydrolysis of the algal biomass.

The methods and systems generally involve the treatment the biomass waste that is produced when lipids (or other products) are extracted from algae. As such, the systems and method of the invention are usually integrated into an algae growth/lipid extraction system or method, many of which are known: See, for example, U.S. Pat. Nos. 4,320,594; 4,253,271; 7,732,170, 7,777,098 and 7,695,626, the complete contents of which are herein incorporate by reference, and which describe systems and methods for growing algae and for extracting lipids or other products of value therefrom.

According to the present invention, as illustrated in FIG. 1, the "waste" that is produced from such processes is subsequently treated as described herein. The first step of the method is hydrolysis of lipid extracted algae waste. By "lipid extracted algae waste" we mean both solid and liquid residues remaining subsequent to the extraction of lipid (or other products) from algal biomass. However, use of the present method need not be confined to agricultural endeavors or to the treatment of lipid extracted algae waste. Other types of waste products such as the organic fraction of municipal solids or combinations thereof with manures may also be processed by the methods of the invention. In particular embodiments, wastes with high carbon/nitrogen (C/N) ratios may be co-hydrolyzed or co-digested with lipid extracted algae waste. The efficient integrated methods and systems of the invention may be adapted and used in any situation where there is a need treat organic waste.

1. Hydrolysis

After lipid extraction the remaining significant portions of the biomass are composed of polysaccharides and proteins. To various degrees these macromolecules are sometimes poorly degraded during a limited AD process, particularly cellulose. The present invention incorporates a step of pretreating the algae biomass waste by hydrolysis prior to AD. Generally, hydrolysis of the cellulose is carried out by methods known to those of skill in the art, including but not limited to using various chemical, mechanical and biological means (e.g. using organisms that digest cellulose or enzymes from such organisms), or combinations thereof. See, for example, U.S. Pat. Nos. 5,221,537; 5,536,325; 5,597,714; 5,763,254; 6,090,595; 7,785,854; and 7,781,191, the complete contents of each of which are herein incorporated by reference, and the references cited therein. The polysaccharides and proteins materials in algal biomass can also be hydrolyzed by acid, ammonia or enzyme methods.

The dilute acid process uses 0.5% to 2% w/w sulfuric acid at 180° C. to 240° C. for several minutes to several hours. Brink (U.S. Pat. Nos. 5,221,537 and 5,536,325, the complete contents of which are herein incorporated by reference) describes a two-step process for the acid hydrolysis of lignoeellulosic material to glucose. The first (mild) step hydrolyzes the hemicellulose to xylose and other sugars. The Second step hydrolyzes the cellulose to glucose. The low levels of acid overcome the need for chemical recovery. However, the maximum glucose yield is only about 55% of the cellulose, and a high degree of production of degradation products can inhibit the bacteria in AD. In U.S. Pat. No. 5,597,714, the complete contents of which are herein incorporated by reference, a higher concentration of sulfuric acid was used to hydrolyze cellulose and hemicellulose. Hemicellulose hydrolyzed with 25-90% w/w sulfuric acid, the dilute the acid concentration to 20-30% to hydrolyze cellulose. However, it may be difficult to recover the sulfuric acid.

Recently, ammonia percolation and enzyme pretreatment are also reported. Iyer et al. (1996) described an ammonia recycled percolation process (temperature 170° C.; pressure 2.3 MPa; ammonia concentration, 2.5-20%; reaction time, 1 h) for the pretreatment of corn cobs/stover mixture and switchgrass. The efficiency of delignification was 60-80% for corn cobs and 65-85% for switchgrass. Kim et al. (2002) reported the enzymatic digestibility of corn stover treated by the ammonia recycled percolation to be 90% with an enzyme loading of 10 FPU/g-glucan. Ash et al. (2008) used 30% aqueous ammonia soaking switchgrass at atmospheric conditions followed by enzymatic saccharification, resulting in a maximum 72% theoretical production of ethanol.

To overcome the problems of the acid method, cellulose conversion processes have developed using two steps: (1) an ammonia percolation pretreatment at atmospheric pressure, and (2) a treatment comprising enzymatic hydrolysis. A typical treatment by enzymatic hydrolysis is carried out by mixing the substrate and water to achieve a slurry of 5% to 12%, by weight of cellulose, and then adding cellulase enzymes (such as U.S. Pat. No. 5,763,254, the complete contents of which are herein incorporated by reference, and European Patent EP0545958).

In some embodiments, the step of hydrolysis is carried out in the same vessel as that in which subsequent steps of the methods are carried out. However, this need not always be the case. In other embodiments, separate vessels or containers may be used for each step or for two or more steps of the method.

2. Anaerobic Digestion and Power Production

The effluent produced by hydrolysis is then subjected to AD. Several methods of AD have been described, including those in published U.S. patent application 12/132,016 (Jiang et al.) published as US2009-020028, and in U.S. Pat. Nos. 7,556,737 and 6,454,944, the complete contents of each of which are herein incorporated by reference.

Those of skill in the art are familiar with AD and various methods and apparatuses for Carrying out AD of waste. Briefly, AD is a process in which microorganisms break down biodegradable material in the absence of oxygen. Initially, bacteria hydrolyze the insoluble organic polymers (e.g. carbohydrates) in the waste material, thereby making them available for other bacteria. Acidogenic bacteria then convert the hydrolysis products (e.g. sugars and amino acids) into carbon dioxide, hydrogen, ammonia, and organic acids. Acetogenin bacteria then convert the organic acids into acetic acid, along with additional ammonia, hydrogen, and carbon dioxide. Finally, methanogenic bacteria convert these products to methane, which can be recovered as biogas, and carbon dioxide. Anaerobic digestion may be carried out, for example, using a variety of designs and methodologies as described in Metcalf and Eddy (2003). The gaseous methane (biogas) produced by AD contains methane (~50-70%) but is impure due to the presence of contaminants such as $CO_2$ and $H_2S$. The methane content is sufficient quantity thought to combust and be used in modified biogas combined heat and power units or with some biogas scrubbing to produce compressed methane fuel. During AD not only is organic carbon converted to the aforementioned biogas but organic nitrogen and phosphorous are also in-part converted to inorganic forms, in particular ammonia and phosphate, respectively. Considerable research has shown that effluents high in calcium and magnesium concentration lead to the production of amorphous, colloidal phosphate solids bound to the positive charges of the calcium and magnesium ions. Wastewaters with such high metal contents include dairy manure and algal biomass. The importance of this conversion and form is considered in descriptions and processes below.

Of note, optionally, during this AD step, other sources of waste (e.g. other high carbon/nitrogen ratio waste such as corn stalks or other corn waste (e.g. cobs), hay, leaves, rice straw, wheat straw, grass clippings, sawdust, shredded wood waste, waste paper pulp, food processing waste, industrial waste, one or more organic fractions of municipal solid wastes, and manures from any source may also be fed into the AD, together with the hydrolyzed algae biomass, thereby providing a route for recycling other waste products as well as well as enhancing overall biogas and inorganic nutrient yield.

3. Nutrient Recovery

A. Phosphorous Recovery

Phosphorous recovery can be achieved in a variety of ways, all of which are encompassed by the present invention. In one embodiment, the P is recovered by coagulation as follows: Coagulants with charges opposite those of the suspended solids are added to the water to neutralize the negative charges on dispersed non-settled solids such as insoluble phosphates and color-producing organic substances. Examples of coagulants typically used in the wastewater industry include ferric and aluminum salts because of their large positive charge. Polymers are often co-dispersed with the coagulants as the polymers can assist in further intensifying the flocculating process once coagulation has occurred. Use of coagulants and polymers while effective and commonplace in municipal wastewater systems is prohibitively expensive in farm-based operations as is envisioned in commercial algal growth facilities in one embodiment, solids which remain after digestion are allowed to settle from the AD effluent. This step may be enhanced, e.g. by the addition of settling agents or "flocculants" such as biopolymers. The settled solids are separated from the supernatant (e.g., the supernatant may be pumped off or the solid sludge may be pumped away) and the solids may be used as fertilizer (e.g., P rich organic fertilizer). This P rich fertilizer is advantageous not just because of its high concentration of desired P, but in that it also contains within its solid matrix other important nutrients including organic nitrogen, potassium and fibrous organic carbon.

Phosphate-rich solids may be removed from the AD effluent using any of a variety of known settling techniques. Depending on the type and condition of waste that is being treated, it may be advantageous to also carry out an initial mechanical separation (e.g. belt press, slope screen, etc.) step to remove large solids and particulate matter prior to solid settling. Settling of solids may be carried out by any of other common biological or chemical methods that are known to those of skill in the art. In one embodiment of the invention, a Chemical procedure is used, examples of which include but are not limited to settling, flocculation, precipitation, electro-coagulation, struvite crystallization, etc.

In the preferred embodiment, prohibitive costs incurred by coagulant and/or polymer addition can be avoided. It is well known that during AD digestion significant amounts of $CO_2$ and even some $CH_4$ produced during the biological process can become dissolved and/or super-saturated within the effluent. This is particularly true of $CO_2$ which is stored within the liquid effluent as $CO_2$ (dissolved), $H_2CO_3$, bicarbonates and carbonates. Upon release from the digester, changes in temperature, pressure, pH, air and agitation can lead to a release of these super-saturated gases (Battistoni et al., 1997; Cecchi et al., 1994). According to Henry's law, $CO_2$ will release to the atmosphere the $CO_2$ partial pressure is lowered through infusion of other gases such as ambient air, thus stripping out supersaturated $CO_2$. As the $CO_2$ partial pressure air is much lower than that of AD, aeration will remove the supersaturated $CO_2$. Removal of the $CO_2$ is advantageous as research has shown that the colloidal phosphate salts stay suspended more from interference from and adhesion to the supersaturated gases that because of charge occurrences Mat are addressed by adding coagulants and polymers. Thus the limited non-biological aeration and its physical-chemical response aids in natural settling and enhanced P removal.

Microscope images of micro-bubbles within liquid AD effluent, showed that these bubbles occur in numbers high enough to disrupt attractive forces with the buoyant forces and micro-turbulence they might induce. To reduce the number of micro-bubbles and thereby reduce their contribution to the suspension of phosphorous particles, the AD effluent is aerated. During aeration, supersaturated $CO_2$ released from liquid phase to gas phase.

In addition, analysis of the chemical balance shows that as aeration releases the gaseous $CO_2$, the reactions all move "towards the right" (see equations 1-4 above), generating more $OH^-$ and raising the pH of the solution, especially with elevated solution temperature. Subsequent testing of this high temperature aeration process verified that the stripping of the $CO_2$ and corresponding elevation in pH also allowed for enhanced ammonia stripping without chemical addition (FIG. 2). Thus, aeration treatment not only leads to the desired P-settling but also N removal through the associated stripping and assumed recovery of the ammonia fraction of the N in the effluent—yielding a truly integrated nutrient recovery process. Notably, the process requires no chemical input, instead relying solely on aeration and temperature, both which can be supplied using only waste-engine exhaust heal and parasitic electricity from the digester.

B. Nitrogen Recovery

Ammonia is in a natural equilibrium with its ionic and free or gaseous forms. With a pKa around 9.5, the equilibrium strongly shifts in favor of free or gaseous form at or above this point with the shift being intensified with increasing temperature. Since AD shifts organic nitrogen to primarily ammonia during its process, it is natural to consider common ammonia stripping operation technology as a means for harnessing the produced ammonia. Unfortunately, commercial systems require the input of alkaline material (lime, lye, etc) to increase the pH well above 9.5. This can be costly especially when the AD process and particular feedstocks such as algal biomass produce and have high levels of alkalinity and natural buffer systems. Thus in order to economically strip ammonia a means for elevating pH without costly chemical addition is required as has been developed in the aforementioned technology description.

Ammonia stripping is a simple desorption process that is used within wastewater treatment industries, and research has confirmed that it is a valuable and reliable ammonia removal technology (Liao et al., 1995; Siegrist, 1996; Cheung et al., 1997; Katehis et al., 1998; Bonmati et al. 2003; Siegrist et al., 2005; Zeng et al., 2005). Briefly; stripping is a distillation procedure that consists of separating fluid components by differences in boiling point or vapor pressure. The usual means of separation is through a column or tower that is packed with one or more various support materials, i.e. Pall Rings, Raschig Rings, Berl Saddles, etc., to increase contact surface. A stripping medium (e.g. hot air or steam, or, in one embodiment of this invention, unheated air) is injected into the bottom of the tower and an ammonia containing solution is injected at or near the top. As the ammonia containing liquid trickles down through the packing, it contacts the rising hot vapor and the more volatile ammonia fraction is vaporized and can be collected and further treated. The less volatile liquid component becomes increasingly purer as it nears the bottom of the tower, where it may be collected.

The stripped ammonia cannot be released to the environment and one traditional means for recovery and use is to perform a secondary stripping operation whereby the ammonia-laden air from the aeration process is reacted with sulfuric acid, allowing the ammonia to preferentially release from the air and enter the acidic solution producing slurry of ammonia sulfate ions. This slurry can then be sold us a bio-fertilizer replacing fossil-fuel based synthetic ammonia sulfate. Solubility curve calculations show that the theoretical Maximum achievable concentration of ammonium sulfate within the slurry is 40% by weight.C. Water reclamation Water is also reclaimed during the nutrient recovery process. Typically, at least about 50%, and usually at least about 60, 70, 80 or even 90% (or more, e.g. 95%) of the water is reclaimed. Reclaimed water may be used for any suitable purpose, and is advantageously recycled back into the system, e.g. is reused in hydrolysis and/or for anaerobic digestion and/or for algae growth. Aeration of the effluent, as described above, increases the pH. e.g. to about 10, and thus makes the high pH water especially suitable for use in hydrolysis Reuse of the reclaimed water reduces costs and requirements of handling, transporting etc. and removal of the water helps to concentrate the other remaining nutrients (P, N) which are thus easier to handle and transport since they are in a smaller volume.

Integrated Systems

The steps for dealing with waste biomass described herein will generally be integrated into a larger biomass generating system. The exemplary integrated system described here is an algae growth system, but those of skill in the art will recognize that the steps of the present method may also be incorporated into other biomass waste generating systems, and/or that other biomass waste may be moved into the system e.g. by addition to the hydrolysis reaction (if the biomass waste contains cellulose), or by addition to the AD reaction (generally high C/N ratio waste). An exemplary algae growth system which incorporates the steps of the present invention includes at least the following components:

1. A reactor or other means or container for growing algae;
2. Means for extracting one or more products of interest (e.g. lipids such as polyunsaturated fatty acids) from the algae and thus producing lipid-extracted algae biomass;
3. A reactor or other or other means or container for containing the lipid-extracted algae biomass during a step of hydrolysis;
4. A reactor or other means or container for carrying out AD of the hydrolyzed lipid-extracted algae biomass produced in 143;
5. One or more reactors or other means or containers for carrying out the various steps of nutrient recovery and/or for collecting the various products, by-products, effluents, etc. which are produced in each step.

One of skill in the art will recognize that some of these steps may be carried out in multiple containers or in the same container by simply adjusting conditions within, e.g. by removing or draining various fractions such as supernatants; precipitants, etc. or by adding various necessary components, e.g. by piping in liquid nutrients or by adding solid components, etc. Further, the temperatures may be adjusted within each container that is used or differentially adjusted in a single container to accord with a particular step or procedure.

The method steps of the invention are described in detail above and are presented in an order that coincides with one embodiment of the invention. However, one advantage of the invention is that it is inherently flexible with respect to the order in which the various steps are carried out, and may be adapted or tailored to meet individual needs or capabilities of the user. The inherent flexibility arises at least: in part from the use of at least one lime settling step to remove solids, and the use of trays and/or media that are capable of handling relatively high concentrations of solids, as compared to other known processes. The ability to handle high amounts of solids during ammonia stripping allows added flexibility regarding the ordering of the steps of the method. For example, in some embodiments, the removal of high phosphate solids is carried out after ammonia stripping. Alternatively, one or more steps of high P solid removal may be carried out prior to ammonia stripping, and one or more additional steps of high P solid removal may be carried out after ammonia stripping. Various other permutations will occur to those of skill in the art, and all such variations are intended to be encompassed by the invention. Similarly, the elements of the integrated system may be set up in any of several variant configurations as required, in order to accommodate the method steps in whatever order, and/or with as many repetitions of one or more steps, as desired.

Exemplary Nutrient Recovery Integration with Algae Growth Systems

There are natural synergies that can be found within the integration of algae growth and AD. For example AD produces heat, $CH_4$, and other chemical nutrients needed for algae growth. However generally these AD byproducts require extraction and/or conversion to be directly utilized for algae growth. For example the methane can be combusted in a engine/turbine to yield heat, electricity and $CO_2$ all of which can be utilized directly in algae growth. Similarly, the integration of nutrient recovery facilitates the use of AD byproducts within algae growth systems.

The integration of conventional AD with algae growth and extraction systems provides, an optimal solution for nutrient and water recycling. Nutrient extraction facilitates a de-coupling of the nutrient and water cycles thereby enabling selective application of nutrients to algal growth media. This independent handling of water and nutrient also alleviates potential inhibitory effects associated with the use of AD wastewater in algae growth media. In the preferred embodiment nutrients recovered from the AD effluent can be used as a process co-product for independent sale or as nutrient for use in growth media, while the nutrient stripped water can be recycled into the hydrolysis pre-treatment process and/or as reclaim water back to the algal growth facility but at the lower levels not resulting in photo-induced inhibition.

Lastly, there is the use of key by-products from the system to induce required chemical, biological and physical transformations without the need for introducing costly external inputs. This is most dramatically seen in the applications of the nutrient recovery and hydrolysis unit operations as well as the above discussed application to algal growth. In the nutrient recovery, the need for alkaline inputs as well as coagulants and polymers is removed through the simple inputs of ambient air, waste heat and gravity settling. In regard to hydrolysis, the need for expensive enzymes, and/or acids and bases is supplanted by the use of existing ammonia, effluent and waste heat resources resulting from the other unit operations.

In summation the complete integrated process is as follows with reference to FIG. 3:

1. 1. Lipid removed algal biomass 4 is sent to a hydrolysis reactor 5 that can operate on any number of known hydrolytic processes but preferably operates as a Modified aqueous ammonia soaking system supplied by system waste heat, system recovered ammonia, and high pH effluent;
2. The resulting hydrolysate is sent to an AD unit 7 of any commercially-available design for production of biogas 9 and inorganic nutrients contained within the effluent. Resulting biogas can be used to produce combined power 11 and heat 12 and/or fuel 13 through known technologies 10;
3. The resulting AD effluent 14, enriched in ammonia and colloidal phosphate salts is treated in a nutrient recovery unit, preferably the described aeration stripping system whereby waste engine heat 12 and ambient air 17 are used to complete a limited non-biological aeration of the effluent. The result is stripped $CO_2$ and ammonia as well as a liquid effluent with reduced supersaturated gases;
4. The resulting liquid effluent 29 is sent to a quiescent zone 30 where colloidal phosphate-rich solids along with some residual organic particles can settle out to produce saleable organic certified phosphate-rich bio-fertilizers 31. Various technologies for dewatering can be used to produce different degrees of solids content;
5. The stripped gases are separated by membrane into two zones whereby the majority of stripped gases in the first zone 21 (mixture of $CO_2$ and ammonia) are sent to an acid tower 23 for production of ammonia salts 28 and a waste $CO_2$ gas stream 24. The stripped gas from the second zone 22 (ammonia and less $CO_2$) is partly or totally sent to the hydrolysis unit 5 for use in the modified aqueous ammonia soaking system;
6. The two produced bio-fertilizers, P-rich solids 31 and ammonia salts 28 can then be dosed into algal growth systems 1 for controlled growth without concomitant addition of potential inhibitors through otherwise addition of the entire effluent waste stream;
7. The final liquid effluent 33 can be directed to two operations, either as nutrient-rich, pathogen controlled reclaimed water for heterotrophic/mixotrophic algal growth operations 34 or as high pH reclaimed water for the hydrolysis 5 and AD 7 operations;
5. Waste $CO_2$ from both the acid towers 24 and the AD engines 10 can be used as feed to the algal growth systems 1.

Thus, substantially all components of the system at each step, (i.e. all products, byproducts, etc.) are used and/or reused, and little or no waste is formed, and waste disposal is moot. In return only limited cost-associated inputs are placed into the system significantly reducing operating costs while also improving upon yield and efficiency.

Figure 3:
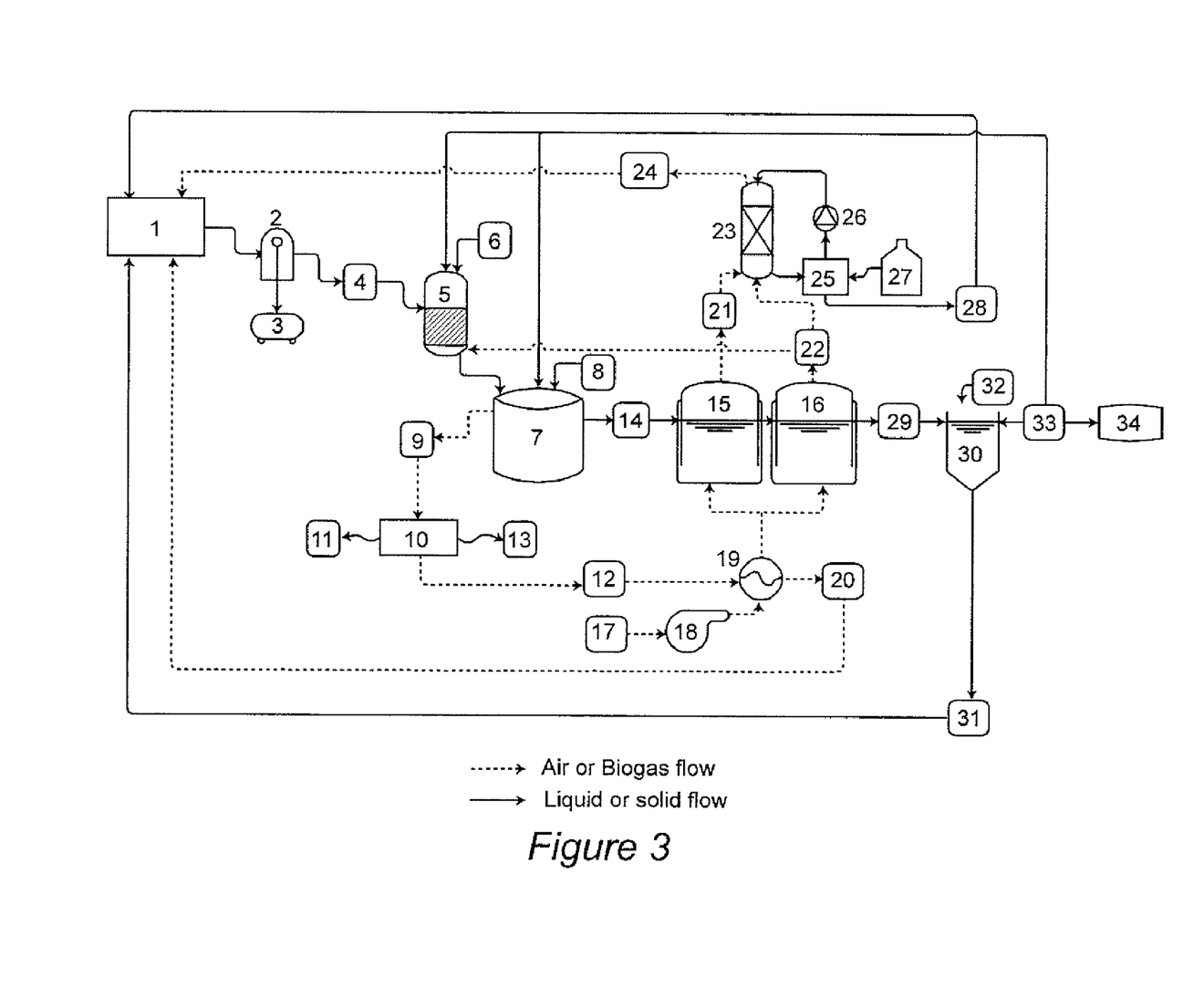
FIG. 3. Schematic of the nutrient recovery system of the invention, incorporated into an algae growth system.

For the convenience of the reader, Table 1 lists all components of the systems depicted in FIG. 3.

TABLE 1

List of System Components 1. algae growth system
2. lipid or other products extraction unit
3. lipid or other products from algae
4. algal biomass after extraction
5. hydrolysis reactor
6. enzyme
7. anaerobic digester
8. high C:N ratio waste
9. biogas
10. known knowledge for producing power, heat and/or fuel from biogas
11. electricity/power
12. waste exhaust heat from engine/generator
13. fuel or other products from biogas
14. AD effluent
15. first aeration zone
16. second aeration zone
17. ambient air
18. air blower
19. heat exchanger
20. cooled engine exhaust with $CO_2$
21. exhaust air from first aeration zone
22. exhaust air from second aeration zone
23. acid tower
24. exhaust air from acid tower
25. ammonium salts storage tank
26. acid pump
27. acid
28. ammonium salts
29. aerated AD effluent
30. Settling zone
31. phosphate-rich bio-fertilizers
32. Coagulant
33. aerated and settled AD effluent
34. heterotrophic/mixotrophic algae growing system with treated AD effluent While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Bonmati, A., Flotats, X. Air stripping of ammonia from pig slurry: characterisation and feasibility as a pre- or post-treatment to mesophilic anaerobic digestion. Waste Management, 23(2003): 261-272.

Battistoni P., Fava G., Pavan P., Musacco A., Cecchi F. Phosphate removal in anaerobic liquors by struvite crystallization without addition of chemicals. Preliminary results. Water Research, 31(1997): 2925-2929.

Cecchi. F. Battistoni P., Pavan P., Fava G., Mata-Alvarez J. Anaerobic digestion of OFMSW and BNR processes: a possible integration. Preliminary results. Water. Science & Technology, 30(1994): 65-71.

Cheung, K. C., Chu, L. M., Wong, M. H. Ammonia stripping as a pretreatment for landfill leachate. Water Air and Soil Pollution, 94 (1997): 209-221.

Isli, A., Himmelsbach, J. N., Pometto III, A. L., Raman, D. R., Anex, R. P., Aqueous ammonia soaking of switchgrass followed by simultaneous saccharification and fermentation, Applied Biochemistry and Biotechnology 144 (1) (2008): 69-77

Iyer, P. V., Z. W. Wu, S. B. Kim and Y. Y. Lee, Ammonia recycled percolation process for pretreatment of herbaceous biomass. Appl. Biochem. Biotechnol. 57/58 (1996): 121-132.

Katehis, D., Diyamandoglu, V., Fillos, J. Stripping and recovery of ammonia from centrate of anaerobically digested biosolids at elevated temperatures. Water Environment Research, 70(1998): 231-240.

Kim, T. H., Kim, J. S., Sunwoo, Lee, Y. Y. (2002). In 24th Symposium on Biotechnology for fuels and Chemicals.

Kim, T. H., J. S. Kim, C. Sunwoo and Y. Y. Lee, Pretreatment of corn stover by aqueous ammonia, Bioresource Technology, 90 (2003), pp. 39-47.

Klinke, H. L. Ahring, A. S. Schmidt and A. B. Thomsen, Characterization of degradation products from alkaline wet oxidation of wheat straw, Bioresource Technology, 82 (2002): 15-26.

Liao, P. H., Chen, A., Lo, K. V. Removal of nitrogen from swine manure wastewaters by ammonia stripping. Bioresource Technology, 54 (1995): 17-20.

Liao, W., Liu, Y., Liu, C., and Chen, S. Optimizing dilute acid hydrolysis of hemicellulose in a nitrogen-rich cellulosic material—dairy manure. Bioresource Technology, 94(2004), 33-41.

Metcalf and Eddy (2003). "Wastewater Engineering Treatment and Reuse". Fourth Edition, Mc Graw Hill, New York, USA.

Siegrist, H., Hunziker, W., Hofer, H. Anaerobic digestion of slaughterhouse waste with UF-membrane separation and recycling of permeate CD after free ammonia stripping. Water Science and Technology, 52(2005): 531-536.

Sun Y, Cheng J., Hydrolysis of lignocellulosic materials for ethanol production: a review, Bioresource Technology, 83(2002):1-11.

Zeng, L., Li, X., Liu, J., Jenson, E. Feasibility study of air stripping of ammonia from digested cattle manure ADSW 2005 conference proceedings, (2005): 656-663.

The invention claimed is:

1. A method of recovering and recycling nutrients from lipid-extracted algae biomass, comprising the steps of:
growing lipid-producing algae;
extracting lipids and/or oils from said lipid-producing algae, thereby obtaining a lipid-extracted algae biomass;
hydrolyzing the lipid-extracted algae biomass, thereby forming hydrolyzed algae biomass such that at least a portion of saccharides produced by the hydrolysis of one or more algae cell wall components are recycled back into said step of growing lipid-producing algae;
anaerobically digesting the hydrolyzed algae biomass, thereby forming anaerobically digested effluent such that at least a portion of $CO_2$ produced in said step of anaerobically digesting is recycled back into said step of growing lipid-producing algae;
separating water from the anaerobically digested effluent such that said water is recycled back into said step of hydrolyzing and/or anaerobically digesting; and
recovering one or more nutrients from the anaerobically digested effluent such that at least a portion of recovered phosphorous and nitrogen are recycled back into said step of growing lipid-producing algae,
thereby recycling one or more components of the recovered nutrients and/or waste into a single integrated algae growth processing system.

2. The method of claim 1, wherein said one or more nutrients recovered in said recovering step include phosphorous and nitrogen.

3. The method of claim 1 wherein said separating step separates at least 90% of said water in said anaerobically, digested effluent.

4. The method of claim 1, further comprising the steps of repeating said steps of hydrolyzing, anaerobically digesting, separating and recovering, and using at least a portion of said water separated in a repeated separating step in a repeated step of hydrolyzing or in a repeated step of anaerobically digesting or in both a repeated step of hydrolyzing and a repeated step of anaerobically digesting.

5. The method of claim 1, further comprising the step of aerating said anaerobically digested effluent prior to or during said step of separating and said step of recovering, said step or aerating removing at least some carbonation from one or more of said anaerobically digested effluent or said water.

6. The method of claim 5, wherein, after said step of separating, water separated in said step of separating step has a pH in the range of 9 to 11 and is used in one or more of said repeated step of hydrolyzing or said repeated step of anaerobically digesting.

7. The method of claim 1, wherein said step of hydrolyzing includes a step of manual breakdown of said lipid-extracted algae biomass.

8. The method of claim 1, wherein said step of hydrolyzing includes one or both of chemical hydrolysis of one or more algae cell wall components and enzymatic hydrolysis of one or more algae cell wall components in said lipid-extracted algae biomass.

9. The method of claim 8 wherein said one or more algae cell wall components is cellulose.

10. The method of claim 9, wherein said chemical hydrolysis of cellulose and said enzymatic hydrolysis of cellulose produces saccharides.

11. The method of claim 10, wherein said saccharides are used for growth of lipid-producing algae.

12. The method of claim 1, wherein, during said step of anaerobically digesting, one or more high carbon/nitrogen ratio waste products are anaerobically digested together with the hydrolyzed algae biomass.

13. The method of claim 12, wherein said one or more high carbon/nitrogen ratio waste products is selected from the group consisting of corn stalks, hay, leaves, rice straw, wheat straw, waste paper pulp, food processing waste, industrial waste, one or more organic fractions of municipal solid wastes, and manures.

14. The method of claim 1, further comprising the step of aerating the anaerobically digested effluent.

* * * * *